DEFENSIVE PUBLICATION

UNITED STATES PATENT AND TRADEMARK OFFICE

Published at the request of the applicant or owner in accordance with the Notice of Dec. 16, 1969, 869 O.G. 687. The abstracts of Defensive Publication applications are identified by distinctly numbered series and are arranged chronologically. The heading of each abstract indicates the number of pages of specification, including claims and sheets of drawings contained in the application as originally filed. The files of these applications are available to the public for inspection and reproduction may be purchased for 30 cents a sheet.

Defensive Publication applications have not been examined as to the merits of alleged invention. The Patent and Trademark Office makes no assertion as to the novelty of the disclosed subject matter.

PUBLISHED SEPTEMBER 2, 1975

938 O.G. 9

T938,012

PREPARATION OF OLEFINS

Gaylord G. Greenfield, Montville, N.J., and Ralph T. Ferrell, Norman, Okla., assignors to Continental Oil Company, Ponca City, Okla.

Filed Sept. 26, 1974, Ser. No. 509,575

**Int. Cl. C07c *3/10***

U.S. Cl. 260—683.15 D

No Drawing. 11 Pages Specification

This disclosure concerns an integrated process for preparing olefins wherein the process includes a dimerization step in conjunction with the conventional "one-step" or sequential processes of preparing linear olefins, wherein the intermediate weight olefins are recycled to the dimerization step. The process serves to increase the amount of high molecular weight (i.e., $C_{12}+$) olefins. Advantages of the integrated process are catalyst sharing and an improvement in product distribution (increasing the amount of higher olefins and decreasing the amount of lower olefins). A particular advantage of the integrated sequential-dimerization process is the use of $C_6$–$C_{10}$ aluminum trialkyls as the catalyst in the dimerization step. These $C_6$–$C_{10}$ aluminum trialkyls can be recovered and recycled to the growth reactor. The overall result is reduced formation of trimers in the dimerization step and a pronounced synergism in the amount of $C_6$–$C_{10}$ olefins produced from the integrated process.